United States Patent
Laizure, Jr.

(10) Patent No.: US 8,292,621 B2
(45) Date of Patent: Oct. 23, 2012

(54) DENTAL HEALING ABUTMENT

(75) Inventor: Robert S. Laizure, Jr., Surprise, AZ (US)

(73) Assignee: ProCerex Dental Lab LLC, Glendale, AZ (US)

( * ) Notice: Subject to any disclaimer, the term of this patent is extended or adjusted under 35 U.S.C. 154(b) by 331 days.

(21) Appl. No.: 12/707,244

(22) Filed: Feb. 17, 2010

(65) Prior Publication Data
US 2011/0200967 A1 Aug. 18, 2011

(51) Int. Cl.
*A61C 13/12* (2006.01)
(52) U.S. Cl. .................................. 433/172; 433/173
(58) Field of Classification Search ....... 433/168.1–175, 433/26
See application file for complete search history.

(56) References Cited

U.S. PATENT DOCUMENTS

| | | | |
|---|---|---|---|
| 5,035,619 A * | 7/1991 | Daftary | 433/173 |
| 5,073,111 A | 12/1991 | Daftary | |
| 5,145,372 A * | 9/1992 | Daftary et al. | 433/173 |
| 5,417,568 A | 5/1995 | Giglio | |
| 5,439,381 A * | 8/1995 | Cohen | 433/173 |
| 5,476,382 A | 12/1995 | Daftary | |
| 5,492,471 A * | 2/1996 | Singer | 433/172 |
| 5,651,675 A * | 7/1997 | Singer | 433/172 |
| 5,674,069 A | 10/1997 | Osorio | |
| 5,759,036 A * | 6/1998 | Hinds | 433/214 |
| 5,813,858 A * | 9/1998 | Singer | 433/173 |
| 5,871,358 A | 2/1999 | Ingber et al. | |
| 5,873,722 A | 2/1999 | Lazzara et al. | |
| 5,899,695 A * | 5/1999 | Lazzara et al. | 433/173 |
| 5,899,697 A * | 5/1999 | Lazzara et al. | 433/173 |
| 5,938,443 A * | 8/1999 | Lazzara et al. | 433/173 |
| 6,012,923 A | 1/2000 | Bassett et al. | |
| 6,042,073 A * | 3/2000 | Moyer et al. | 248/346.01 |
| 6,120,293 A | 9/2000 | Lazzara et al. | |
| 6,155,828 A | 12/2000 | Lazzara et al. | |
| 6,171,106 B1 * | 1/2001 | Kaneko et al. | 433/173 |
| 6,227,856 B1 | 5/2001 | Beaty et al. | |
| 6,244,868 B1 * | 6/2001 | Schappert | 433/173 |
| 6,299,447 B1 * | 10/2001 | Zuest et al. | 433/172 |
| 6,386,876 B1 | 5/2002 | Lee | |
| D487,153 S | 2/2004 | Schulter et al. | |
| D493,890 S | 8/2004 | Schulter et al. | |
| 7,179,089 B2 | 2/2007 | Sims et al. | |
| 2002/0064758 A1 | 5/2002 | Lee | |
| 2003/0013068 A1 | 1/2003 | Gittleman | |
| 2003/0228555 A1 | 12/2003 | Morgan | |
| 2009/0155744 A1 | 6/2009 | Jandali | |

FOREIGN PATENT DOCUMENTS
WO 2008016917 2/2008

OTHER PUBLICATIONS
European Search Report for European Application No. 11154162.9; dated May 27, 2011; six (6) pages.

* cited by examiner

*Primary Examiner* — Cris L Rodriguez
*Assistant Examiner* — Matthew Saunders
(74) *Attorney, Agent, or Firm* — Gerald E. Hespos; Michael J. Porco

(57) ABSTRACT

A dental healing abutment assembly having a tubular holder and a plurality of removable nestable shells. Each nestable shell has a proximal end and a distal end open to permit the nesting of the shell with the holder or other nestable shells. The proximal end of each nestable shell is defined by a base plate. The tubular holder and the nestable shells each have a pass through hole for accommodating a mounting member. The healing abutment assembly is attached to a dental implant impacted in a patient's jawbone by way of the mounting member.

20 Claims, 4 Drawing Sheets

DENTAL HEALING ABUTMENT

FIELD

The present disclosure relates generally to the field of dental implants and in particular to a healing abutment customizable in emergence profile and size.

DESCRIPTION OF THE PRIOR ART

Single tooth dental implant systems are well known in the prior art. An important system for replacing a single tooth is comprised of several parts, namely, an implant, at least one abutment, and a prosthesis. First, the implant is placed into the jawbone. The implant is generally a threaded metal member that acts as a root for the eventual prosthesis, or crown. The implant fuses to the jawbone through osseointegration. This process can take as long as six months. The implant is generally cylindrical with a threaded hollow opening extending in a longitudinal direction.

A second procedure may be required for placement of a healing abutment. An incision is made in the gingival tissue to expose the implant. A healing abutment is threadably engaged with the implant. The healing abutment allows gingival tissue to heal prior to the placement of a permanent abutment. In addition, the healing abutment maintains proper spacing in the oral cavity before the prosthesis is placed. After the gingival tissue heals around the healing abutment, the healing abutment is removed and replaced with a permanent abutment. At this point, the gingival tissue again may be given an opportunity to heal around the permanent abutment and a temporary cap may be placed on the permanent abutment for aesthetic purposes. Next, a prosthesis is molded to fit onto the permanent abutment and between surrounding teeth. The prosthesis is affixed to the abutment through any known means, such as adhesive, a screw, or other mechanical means. U.S. Pat. No. 5,073,111 provides an example of this state of the art.

Healing abutments are well known in the prior art. However, the prior art does not disclose healing abutments that are adjustable in terms of size and emergence profile. Rather, the prior art requires dentists to maintain an inventory of plural abutments of varying size and emergence profile to account for natural variations in the shape and size of dental cavities in different patients. The inventory management of abutments of different shapes and sizes is costly and complicated. Thus, it would be desirable to have a healing abutment assembly that avoids the costs and complications of the prior art.

SUMMARY

The present disclosure relates to a healing abutment assembly, and to a dental implant system that includes a healing abutment assembly. The healing abutment assembly has removable layers that allow for customization in emergence profile and size.

The healing abutment assembly of the present disclosure may include or be used with a dental implant. The dental implant has a first end and a second end, the second end being defined by an opening, that may include an array of internal threads. The first end is configured to be implanted through the gingival tissue and into the alveolus of the jaw bone. The opening in the second end may be closed selectively by a cap or other known means. The implant is configured to permit the jawbone to grow around the implant, thereby permanently holding the implant in an impacted position. For example, the outer surface of the implant may be textured or coated in a manner that will promote bone ingrowth.

After the implant is secured to the jawbone through osseointegration, a healing abutment assembly is secured to the implant. The healing abutment assembly preferably comprises a holder that may be substantially tubular. The holder has a first end, a second end, an outer surface, and an inner surface. The inner surface defines a hollow portion that traverses the holder in a longitudinal direction from the first end to a position substantially near the second end. The hollow portion preferably is substantially centered along a longitudinal axis of the holder. A flange preferably extends in from the inner surface of the holder adjacent to the second end to define an opening. The diameter of the opening is less than the diameter of portions of the hollow portion adjacent to the first end and may be substantially equal to the diameter of the opening in the implant.

The healing abutment assembly includes at least one, and preferably several, nestable shells. As used herein, "nestable" refers to the stackable property of the shells that allow them to be combined in a surface-to-surface contact. Each nestable shell has opposite proximal and distal ends. The distal end of each nestable shell is open to receive either the holder or another one of the shells. A base plate extends across the proximal end and is configured to be mounted substantially adjacent the second end of the holder and/or the second end of the implant. The base plate may be substantially circular and may have an outer surface that is circumferentially aligned with the outer surface of the holder and/or the second end of the implant. The base plate also has an opening that can be registered with the opening in the implant. Each nestable shell further has a side wall that flares radially outward from the outer surface of the base plate. The side wall has an inner and an outer surface. The inner surface of the side wall is configured to nest securely with either the outer surface of the holder or the outer surface of another of the nestable shells. The outer surface of the side wall preferably curves upward and flares outwardly from the proximal end to the distal end. The top surface of the side wall is substantially flush with the first end of the holder. The outer surface of at least one of the nestable shells is configured to nest closely with the inner surface of the side wall of another of the nestable shells.

The healing abutment assembly may further include a mounting member, such as a screw, that passes through the opening of the holder and through the openings in the base plates for attachment to the implant.

Each nestable shell may be separated from adjacent nestable shells to adjust the diameter of the healing abutment assembly, allowing a dentist to fit the healing abutment assembly between the surrounding teeth. When the preferred number of nestable shells have been removed, an incision is made in the gingival tissue to expose the second end of the implant. The cap or other closing means is removed from the implant and the screw of the healing abutment assembly is engaged with the hollow opening of the implant, thereby tightly securing the healing abutment assembly in place. The healing abutment assembly remains secured in the implant until the gingival tissue can grow around the healing abutment assembly. In the secured position, a top side of the healing abutment assembly, defined by the distal ends of each side wall and the holder, is covered by gingival tissue.

After the gingival tissue has grown around the healing abutment assembly, a second incision is made in the tissue to expose the healing abutment assembly. The healing abutment assembly is disengaged from the implant and replaced by a permanent abutment. A prosthesis then is affixed to the permanent abutment.

DETAILED DESCRIPTION OF THE PREFERRED EMBODIMENT

All examples and conditional language recited herein are intended for teaching purposes to aid the reader in understanding the principles of the disclosure and the concepts contributed by the inventor to furthering the art, and are to be construed as being without limitation to such specifically recited examples and conditions.

Moreover, all statements herein reciting principles, aspects and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Figure 1:
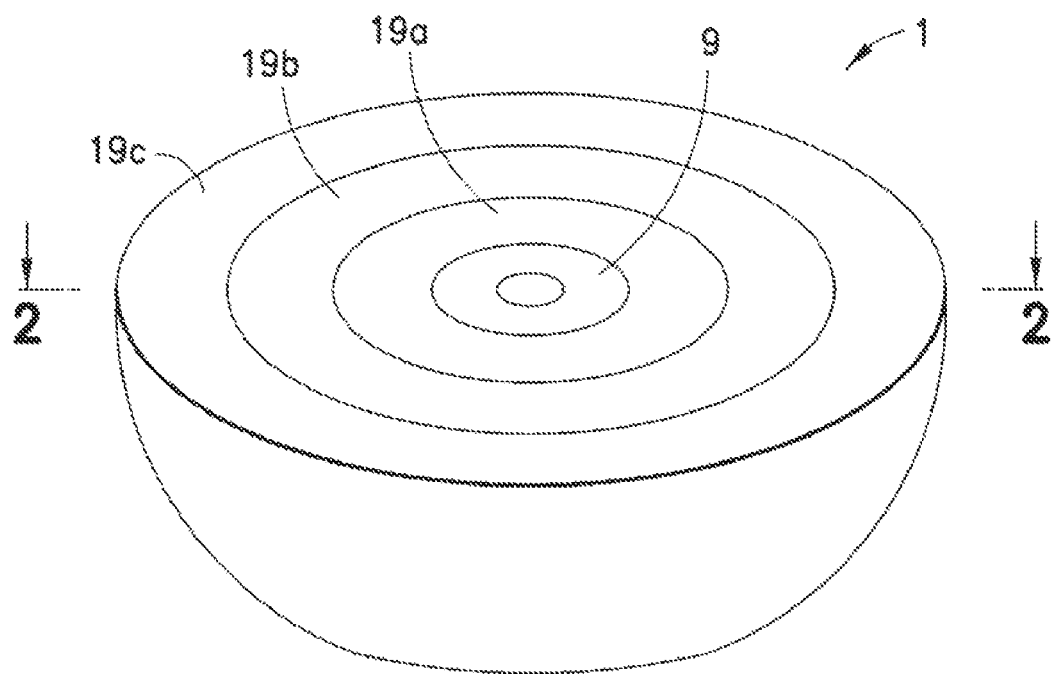
FIG. 1 is a perspective view of the healing abutment assembly.
Figure 2:
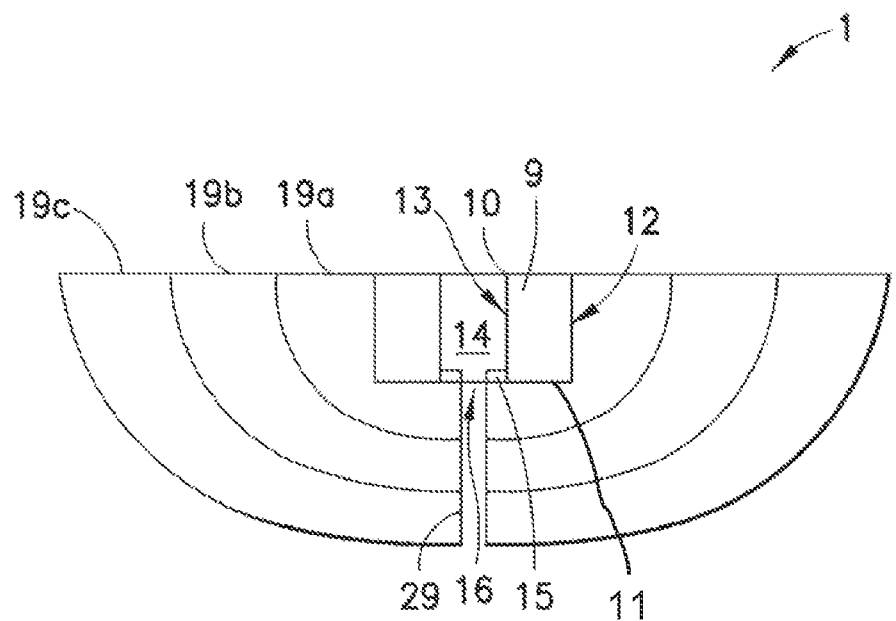
FIG. 2 is a cross sectional view of the healing abutment assembly taken along line 2-2 in FIG. 1 and shows the healing abutment assembly connected to an implant.
Figure 3:
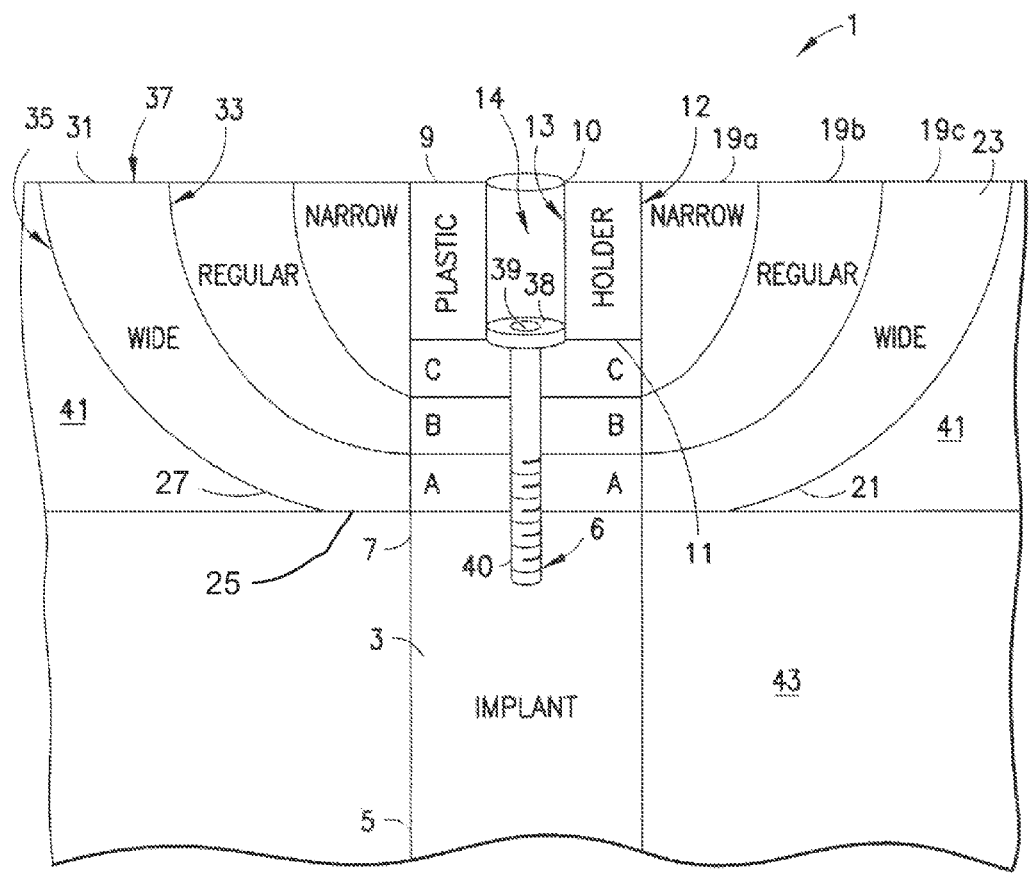
FIG. 3 is a side view of the healing abutment assembly inserted in the dental cavity.

With reference to the drawings, embodiments of the present disclosure will be described. As shown in FIGS. 1-3, a healing abutment assembly 1 is shown having: a holder 9, a plurality of nestable shells 19 and a mounting member 39. The healing abutment assembly 1 of the present disclosure may include or be used with an implant 3. The implant 3 has a first end 5 and a second end 7. The first end 5 of the implant 3 is configured to be implanted through a section of gingival tissue 41 and into the alveolus of a jawbone 43. The second end 7 is defined by an opening 6. In the preferred embodiment, the opening 6 is defined by an array of internal threads. The opening 6 may be closed selectively by a cap (not shown) or other known closure means. The implant 3 is placed in the jawbone 43 by a surgical procedure and is anchored to the jawbone 43 through osseointegration.

After the implant 3 is secured to the jawbone 43, the healing abutment assembly 1 is secured to the implant 3. The healing abutment assembly 1 comprises a substantially tubular holder 9. The holder 9 has a first end 10, a second end 11, an outer surface 12, and an inner surface 13. The inner surface 13 defines a hollow portion 14 traversing the holder 9 in a longitudinal direction from the first end 10 to a position substantially near the second end 11. The hollow portion 14 is substantially centered in the holder 9. A flange 15 extends inward from the inner surface 13 at the second end 11 to define an opening 16 in the second end 11. The diameter of the opening 16 is less than the diameter of the hollow portion 14. The diameter of the opening 16 should be substantially equal to the diameter of the opening 6 in the implant 3.

The healing abutment assembly 1 includes at least one, and preferably several, nestable shells 19a, 19b, 19c. Each nestable shell 19a-c has a proximal end 21 and a distal end 23, the proximal end being closest to the implant 3 and the distal end being further from the implant 3. The distal end 23 of each nestable shell 19a-c is open to permit nesting with the holder 9 or with another of the shells. A base plate 25 having an outer surface 27 extends across the proximal end 21 of each nestable shell 19a-c and is configured to be mounted substantially in registration with the second end 11 of the holder 9. In the preferred embodiment, the base plate 25 is substantially circular and the outer surface 27 is circumferentially aligned with the outer surface 12 of the holder 9. The base plate 25 has an opening 29 that can be registered with the opening 6 in the implant 3 and the opening 16 in the holder 9.

Figure 6:
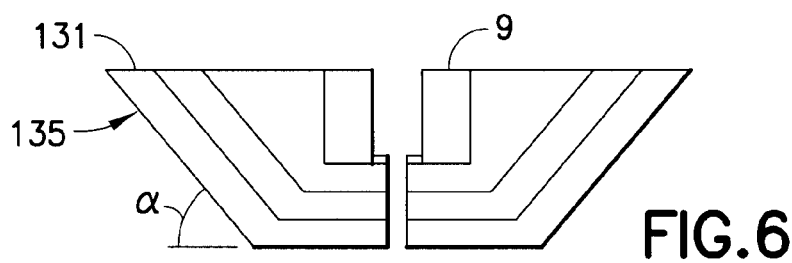
FIG. 6 is a cross-sectional view of a third embodiment of the healing abutment assembly. (conical shells)

Each nestable shell 19a-c has a side wall 31 that extends from the proximal end 21 to the distal end 23, and that flares radially outward from the outer surface 27 of the base plate 25. The side wall 31 has an inner surface 33 and an outer surface 35. The inner surface 33 of the side wall 31 is configured to nest securely with either the outer surface 12 of the holder 9 or the outer surface 35 of another of the nestable shells 19a-c. In the preferred embodiment, the outer surface 35 of the side wall 31 curves upward and flares outwardly. However, in a second embodiment, as shown in FIG. 6, the outer surfaces 135 of the side walls 131 can be conically generated to define a constant linear slope that flares outward from the base plate at an angle between 0° and 90°. The top surface 37 of the side wall 31 is substantially flush with (i.e. coplanar with) the first end 10 of the holder 9. The outer surface 35 of at least one of the nestable shells 19 is configured to nest closely with the inner surface 33 of the side wall 31 of another of the nestable shells 19.

The healing abutment assembly 1 further comprises a mounting member 39, preferably a screw, that passes through the hollow portion 14 of the holder 9. The head 38 of the screw is dimensioned to be substantially larger than the diameter of the opening 16 of the holder 9. The threaded portion 40 of the mounting member 39 is configured to be threadably engageable with the internal threads 17 of the opening 6 of the implant 3.

Figure 4:
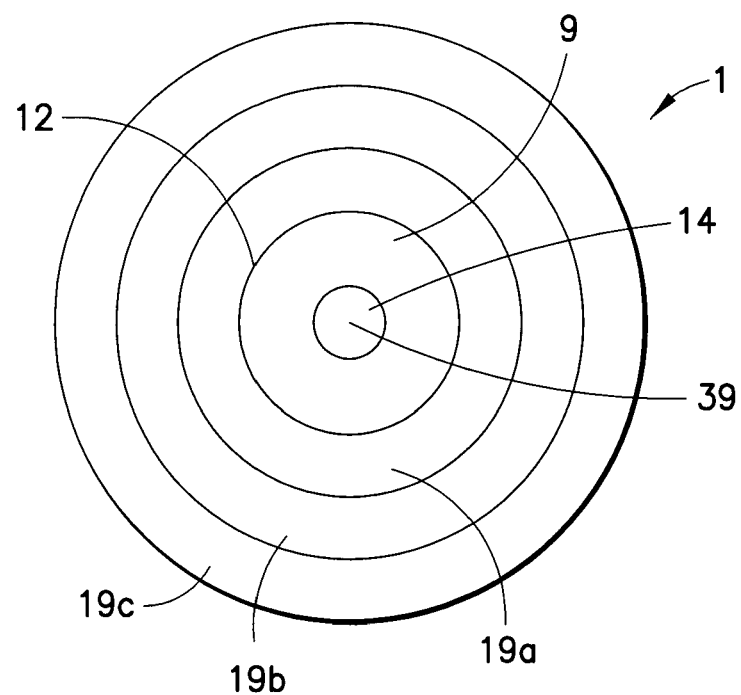
FIG. 4 is a top plan view of the healing abutment assembly.
Figure 5:
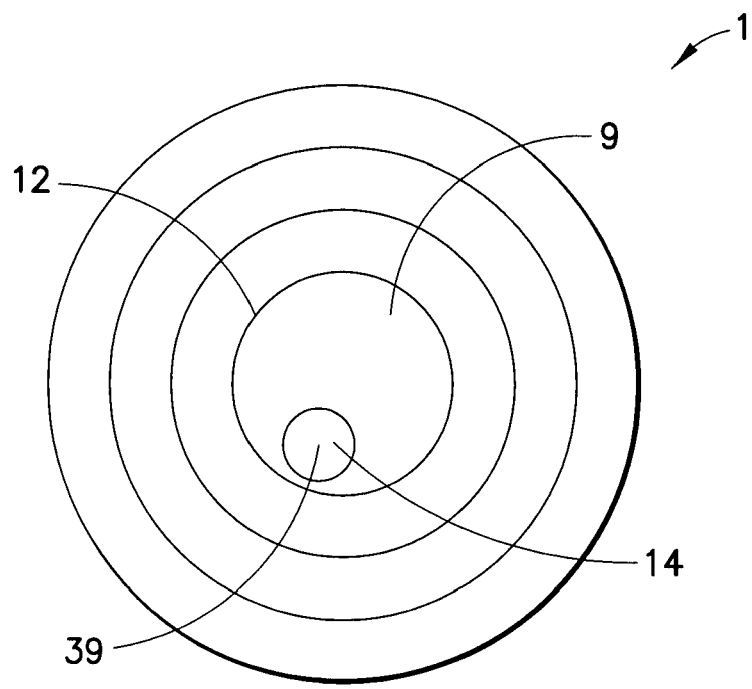
FIG. 5 is a top plan view of a second embodiment of the healing abutment assembly. (referring to the off-center abutment)

In the preferred embodiment, the healing abutment assembly 1 is aligned symmetrically with the implant 3 as shown in FIG. 4. However, in some instances, the implant 3 must be asymmetrically aligned with the healing abutment assembly 1. As shown in FIG. 5, a second embodiment of the invention is provided to allow for attachment of the healing abutment assembly 1 with an asymmetrically aligned implant 3. In this embodiment, the hollow portion 14 and the opening 16 of the holder 9, as well as the openings 29 of the nestable shells 19a-c, are off-center from the longitudinal axis of holder 9 to provide for flexibility in the placement of the healing abutment assembly 1.

In the preferred embodiment, the holder 9 is made of plastic. However, in alternate embodiments, the holder 9 may be formed from any bio-compatible material.

Figure 7:
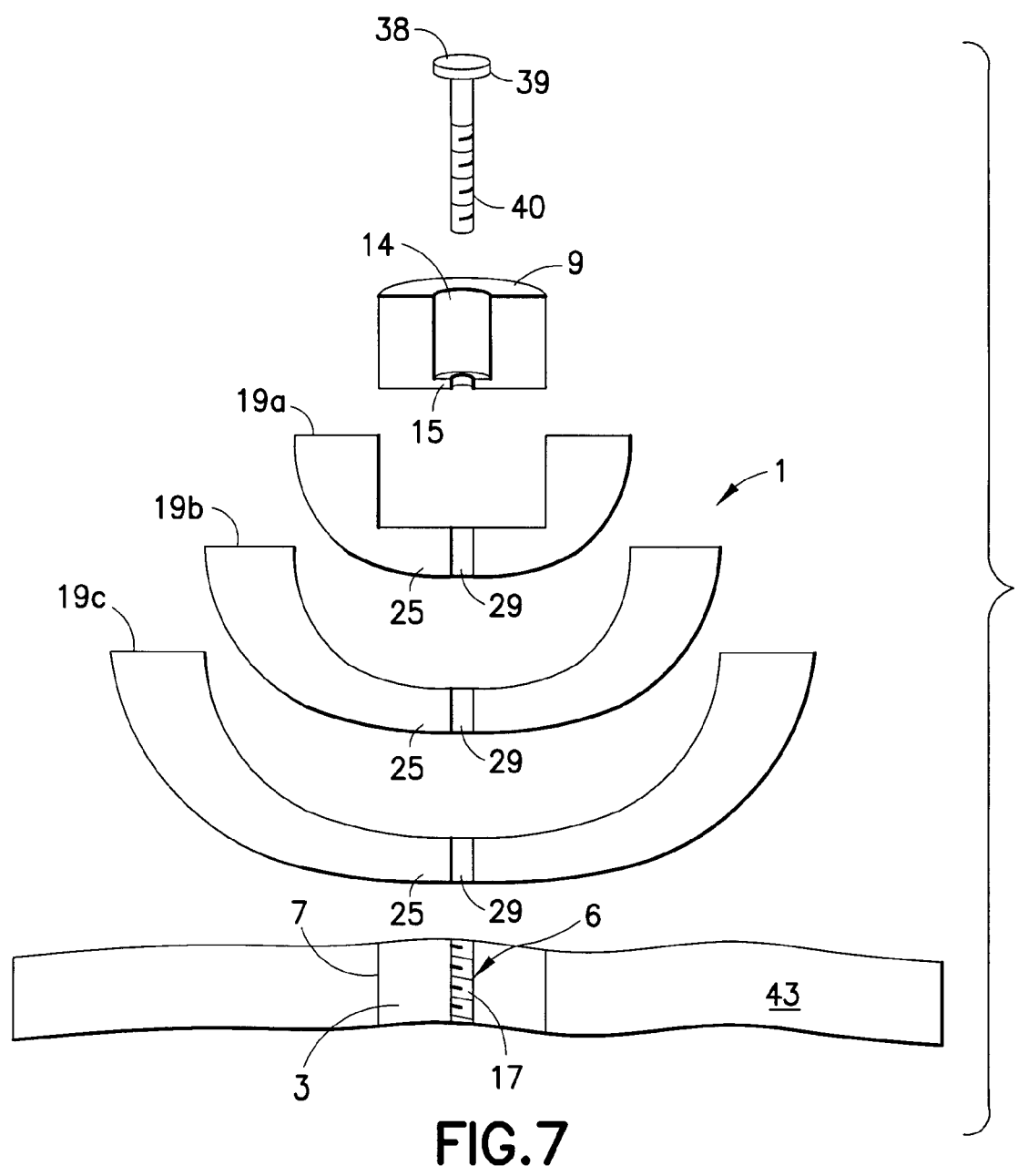
FIG. 7 is an exploded perspective view of the healing abutment assembly.

With reference to FIG. 7, the method of attaching the healing abutment assembly 1 to the implant 3 is herein described. The width of a space where the healing abutment assembly 1 is to be inserted is measured. Based on the width measurement, a dentist determines the preferred emergence profile and size of the healing abutment assembly 1. The dentist adds or removes one or more nestable shell 19 to closely match the preferred width of the healing abutment assembly 1 as determined by the physiology of the patient. The screw 39 is inserted through the hollow portion 14 of the holder 9 so that the threaded portion 40 is inserted through the opening 16 and the opening(s) 29 in the base plate 25 of the nestable shells 19. The threaded portion 40 is next inserted through the opening 6 in the second end 7 of the implant 3.

The screw 39 is engaged with the opening 6 until the healing abutment assembly 1 is securely fastened.

Although the disclosure herein has been described with reference to particular illustrative embodiments, it is to be understood that these embodiments are merely illustrative of the principles and applications of the present disclosure. Therefore numerous modifications may be made to the illustrative embodiments and other arrangements may be devised without departing from the spirit and scope of the present disclosure, which is defined by the appended claims.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . ." or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

What is claimed is:

1. A healing abutment assembly for use with a dental implant, comprising:
   a holder having opposite first and second ends and opposite outer and inner surfaces extending between the ends, the inner surface defining a hollow portion traversing the holder in a longitudinal direction from the first end toward the second end, an inwardly facing flange extending from the inner surface of the holder at a position in proximity to the second end to define an opening that is cross sectionally smaller than the hollow portion; and
   a plurality of nestable shells each having a proximal end and a distal end, the distal end of each said shell being open to permit nesting of the respective shell with the holder or another one of the shells, the proximal end of each of said shell includes a base plate extending across the proximal end and configured to be mounted substantially in registration with the second end of the holder and having an opening that is registered with an opening of the holder, each of said shell includes a side wall extending from the proximal end to the distal end, the side wall having an inner surface and an outer surface flaring radially outward from an outer surface of the base plate, the inner surface of the side wall being configured to nest securely with the outer surface of the holder or the outer surface of another of the nestable shells.

2. The healing abutment assembly of claim 1, further comprising a mounting portion is provided for securing the healing abutment assembly of the implant, wherein the mounting portion is a screw having a head dimensioned to be substantially larger than the diameter of the opening defined by the flange of the holder and a threaded portion engageable with the implant.

3. The healing abutment assembly of claim 1, wherein the hollow portion and the opening of the holder are concentric with a longitudinal axis of the holder.

4. The healing abutment assembly of claim 1, wherein the hollow portion of the holder and the opening are displaced from a longitudinal axis of the implant.

5. The healing abutment assembly of claim 1, wherein the outer surfaces of the side walls flare outward and curve upward from the proximal end to the distal end.

6. The healing abutment assembly of claim 1, wherein the inner surface of the side wall flares outward with a substantially constant linear slope from a proximal end to a distal end and the outer surface of the side wall flares outwardly with a substantially constant slope from a proximal end to a distal end.

7. The healing abutment assembly of claim 1, wherein a mounting portion is provided for securing the healing abutment assembly to the implant.

8. The healing abutment assembly of claim 7, wherein the mounting portion is a screw threadably engageable with the implant.

9. The healing abutment assembly of claim 8, wherein the holder is formed of a bio-compatible material.

10. A healing abutment assembly for use with a dental implant, comprising:
    a holder having opposite first and second ends and opposite outer and inner surfaces extending between the ends, the inner surface defining a hollow portion traversing the holder in a longitudinal direction from the first end toward the second end, an inwardly projecting flange extending from the inner surface of the holder at a position in proximity to the second end to define an opening that is cross sectionally smaller than the hollow portion;
    a first nestable shell having a proximal end, an open distal end and a side wall extending therebetween, the side wall of the first nestable shell having an inner surface nested with the outer surface of the holder and an outer surface opposite the inner surface, a base plate extending in from the side wall at a location in proximity to the proximal end; and
    a second nestable shell having a proximal end, an open distal end, and a side wall extending from the proximal end to the distal end, the side wall of the second nestable shell having an inner surface and an outer surface flaring radially outward from the proximal end to the distal end, the inner surface of the side wall of the second nestable shell being nested removably with the outer surface of the side wall of the first nestable shell.

11. The healing abutment of assembly of claim 10 further comprising a third nestable shell having a proximal end and an open distal end, and a side wall extending from the proximal end to the distal end, the side wall having an inner surface and an outer surface flaring radially outward from the proximal end to the distal end, the inner surface of the third nestable shell being nested with the outer surface of the second nestable shell.

12. The healing abutment assembly of claim 10, further comprising a mounting portion having a head larger than the opening in the flange of the holder and a shaft engageable with the implant.

13. The healing abutment of claim 10, wherein the hollow portion and the opening of the holder are centered along a longitudinal axis of the holder.

14. The healing abutment of claim 10, wherein the hollow portion of the holder and the opening are offset from a longitudinal axis of the implant.

15. The healing abutment of claim 10, wherein the outer surfaces of the side walls of each of the nestable shells flare outward and curve upward from the proximal end to the distal end.

16. The healing abutment of claim 10, wherein the inner surface of the side wall of each of the nestable shells flares outward with a substantially constant linear slope from a proximal end to a distal end and the outer surface of the side wall of each of the nestable shells flares outwardly with a substantially constant slope from a proximal end to a distal end.

17. The healing abutment of claim 10, wherein a mounting portion is provided for securing the healing abutment assembly to the implant.

18. The healing abutment of claim 17, wherein the mounting portion is a screw threadably engageable with the implant.

19. The healing abutment of claim 18, wherein the holder is formed from a bio-compatible material.

20. The healing abutment assembly of claim 1, wherein a top surface of the side wall of each of said shell is coplanar with the first end of the holder.

* * * * *